(12) United States Patent
Iyun et al.

(10) Patent No.: US 10,376,221 B2
(45) Date of Patent: Aug. 13, 2019

(54) AUTOMATIC CREATION OF MULTIPLE ELECTROANATOMIC MAPS

(71) Applicant: BIOSENSE WEBSTER (ISRAEL) LTD., Yokneam (IL)

(72) Inventors: Ofra Iyun, Haifa (IL); Noga Salomon, Haifa (IL); Galia Givaty, Haifa (IL); Eliran Guzi, Haifa (IL); Vladimir Rubinstein, Haifa (IL); Meir Bar-Tal, Haifa (IL); Morris Ziv-Ari, Atlit (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 12 days.

(21) Appl. No.: 15/202,990

(22) Filed: Jul. 6, 2016

(65) Prior Publication Data

US 2018/0008203 A1      Jan. 11, 2018

(51) Int. Cl.
| | |
|---|---|
| A61B 5/0432 | (2006.01) |
| A61B 5/00 | (2006.01) |
| A61B 5/04 | (2006.01) |
| A61B 5/042 | (2006.01) |
| A61B 5/044 | (2006.01) |
| A61B 5/0452 | (2006.01) |
| G09B 23/30 | (2006.01) |
| G09B 23/28 | (2006.01) |
| G16H 50/70 | (2018.01) |
| G16H 50/20 | (2018.01) |

(52) U.S. Cl.
CPC ......... *A61B 5/7275* (2013.01); *A61B 5/044* (2013.01); *A61B 5/04012* (2013.01); *A61B 5/0422* (2013.01); *A61B 5/0452* (2013.01); *A61B 5/6858* (2013.01); *A61B 5/7246* (2013.01); *G09B 23/288* (2013.01); *G09B 23/30* (2013.01); *G16H 50/70* (2018.01); *G16H 50/20* (2018.01)

(58) Field of Classification Search
None
See application file for complete search history.

(56) References Cited

U.S. PATENT DOCUMENTS

| | | | |
|---|---|---|---|
| 4,531,527 A | * | 7/1985 | Reinhold, Jr. ....... A61B 5/0006 128/903 |
| 5,546,951 A | | 8/1996 | Ben-Haim |
| 5,711,305 A | | 1/1998 | Swanson et al. |

(Continued)

FOREIGN PATENT DOCUMENTS

| | | |
|---|---|---|
| EP | 0 809 464 A1 | 12/1997 |
| WO | WO 1995/002995 A1 | 2/1995 |

(Continued)

OTHER PUBLICATIONS

European Search Report dated Nov. 24, 2017 in corresponding European Patent Application No. 17179881.2.

(Continued)

*Primary Examiner* — Kennedy Schaetzle
(74) *Attorney, Agent, or Firm* — Dergosits & Noah LLP; Todd A. Noah

(57) ABSTRACT

Cardiac electrograms are recorded in a plurality of channels. Beats are classified automatically into respective classifications according to a resemblance of the morphologic characteristics of the beats to members of a set of templates. Respective electroanatomic maps of the heart are generated from the classified beats.

18 Claims, 8 Drawing Sheets

(56) References Cited

U.S. PATENT DOCUMENTS

| | | | |
|---|---|---|---|
| 6,101,409 | A | 8/2000 | Swanson et al. |
| 6,226,542 | B1 | 5/2001 | Reisfeld |
| 6,301,496 | B1 | 10/2001 | Reisfeld |
| 6,690,963 | B2 | 2/2004 | Ben-Haim et al. |
| 6,814,733 | B2 | 11/2004 | Yitzhack Schwartz et al. |
| 6,892,091 | B1 | 5/2005 | Ben-Haim et al. |
| 6,997,924 | B2 | 2/2006 | Schwartz et al. |
| 7,156,816 | B2 | 1/2007 | Schwartz et al. |
| 7,242,978 | B2 | 7/2007 | Cao et al. |
| 7,328,063 | B2 | 2/2008 | Zhang et al. |
| 7,536,218 | B2 | 5/2009 | Govari et al. |
| 7,756,576 | B2 | 7/2010 | Levin |
| 7,930,020 | B2 | 4/2011 | Zhang et al. |
| 8,185,195 | B2 | 5/2012 | Kim et al. |
| 8,433,398 | B2 | 4/2013 | Zhang |
| 8,442,624 | B2 | 5/2013 | Zhang |
| 8,478,383 | B2 | 7/2013 | Bar-Tal et al. |
| 8,483,808 | B2 | 7/2013 | Dong et al. |
| 8,583,228 | B2 | 11/2013 | Li et al. |
| 8,977,350 | B2 | 3/2015 | Sarkar et al. |
| 9,380,953 | B2 | 7/2016 | Houben et al. |
| 2007/0197929 | A1 | 8/2007 | Porath et al. |
| 2008/0288009 | A1 | 11/2008 | Kim et al. |
| 2012/0184858 | A1 | 7/2012 | Harlev et al. |
| 2015/0057507 | A1* | 2/2015 | Koyrakh ............ A61B 5/066 600/301 |
| 2015/0073246 | A1 | 3/2015 | Chmiel et al. |
| 2015/0208942 | A1 | 7/2015 | Bar-Tal et al. |

FOREIGN PATENT DOCUMENTS

| | | |
|---|---|---|
| WO | WO 1996/05768 A1 | 2/1996 |
| WO | WO 2006/066324 A1 | 6/2006 |
| WO | WO 2012/092016 A1 | 7/2012 |

OTHER PUBLICATIONS

Bhakta, Deepak MD et al., "Principles of Electroanatomic Mapping", Indian Pacing and Electrophysiology Journal, Feb. 1, 2008, pp. 32-50.

Lozoya, Rocio Cabrera, "Radiofrequency ablation planning for cardiac arrhythmia treatment using modeling and machine learning approaches", HAL archives-ouvertes, Dec. 15, 2015, pp. 10-12 and 30-31.

XP055560784, "Weighted Correlation Matrix".

\* cited by examiner

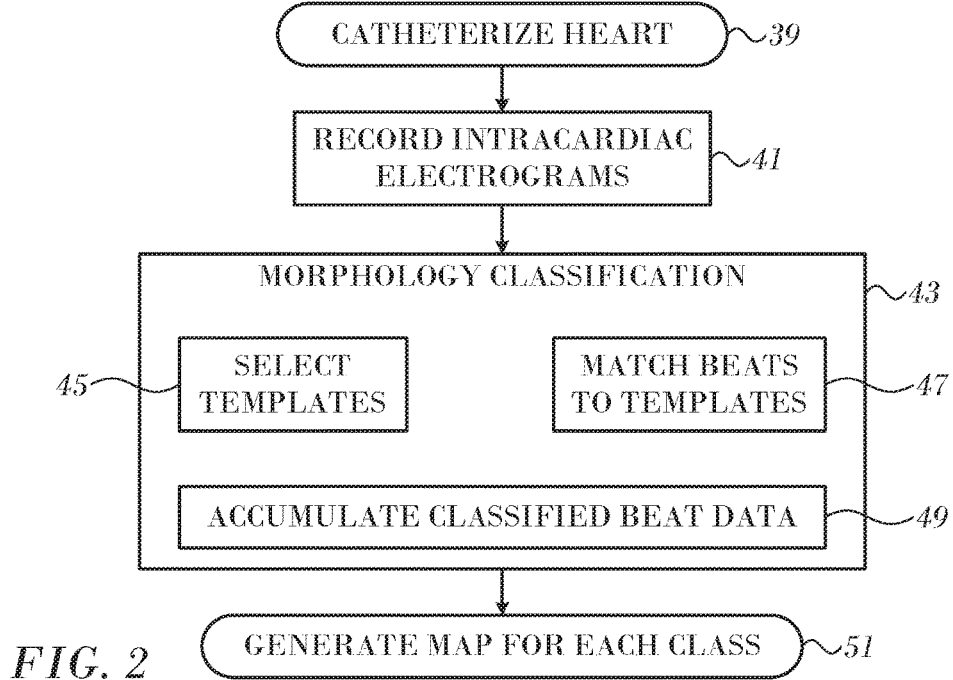
FIG. 2
FIG. 3
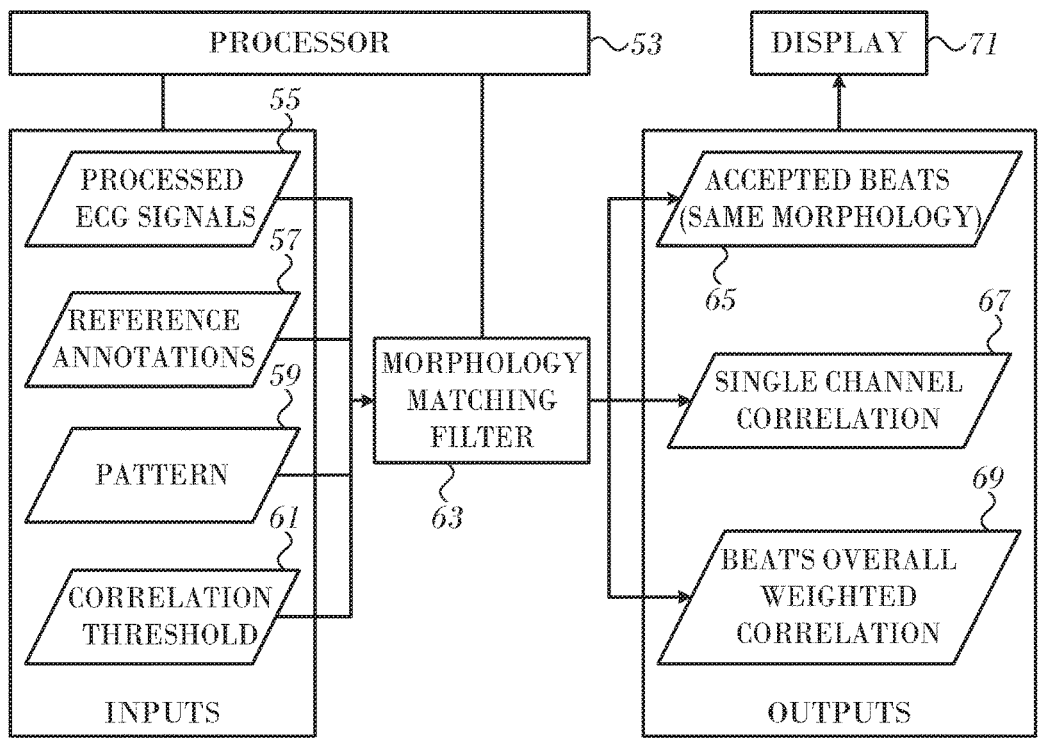

AUTOMATIC CREATION OF MULTIPLE ELECTROANATOMIC MAPS

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to detecting, measuring or recording bioelectric signals of the body. More particularly, this invention relates to generation of electroanatomic maps of the heart.

2. Description of the Related Art

The meanings of certain acronyms and abbreviations used herein are given in Table 1.

TABLE 1

| Acronyms and Abbreviations | |
|---|---|
| LAT | Local Activation Time |
| ECG | Electrocardiogram |

Cardiac arrhythmias such as atrial fibrillation are an important cause of morbidity and death. Commonly assigned U.S. Pat. Nos. 5,546,951, and 6,690,963, both issued to Ben Haim; and PCT application WO 96/05768, all of which are incorporated herein by reference, disclose methods for sensing an electrical property of heart tissue, for example, local activation time, as a function of the precise location within the heart. Data are acquired with one or more catheters having electrical and location sensors in their distal tips, which are advanced into the heart. Methods of creating a map of the electrical activity of the heart based on these data are disclosed in commonly assigned U.S. Pat. Nos. 6,226,542, and 6,301,496, both issued to Reisfeld, which are incorporated herein by reference. As indicated in these patents, location and electrical activity is typically initially measured on about 10 to about 20 points on the interior surface of the heart. These data points are then generally sufficient to generate a preliminary reconstruction or map of the cardiac surface. The preliminary map is often combined with data taken at additional points in order to generate a more comprehensive map of the heart's electrical activity. Indeed, in clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Conventionally, a particular type of arrhythmia, characterized by the signal morphology of the arrhythmia, may be viewed on a single electroanatomic map generated from electroanatomical recordings. Other arrhythmias that are present in the electrical recording are often manually deleted. If the physician detects several morphologies, he may create a mixed map with polymorphic beats and separate them later on by moving points to a new opened map.

SUMMARY OF THE INVENTION

Embodiments of the present invention use the electroanatomical recordings to generate multiple maps of the various arrhythmias that may be present in a set of data. The user may utilize all available data at the same time. Even when mapping a specific arrhythmia, cardiac cycles, (also referred to herein as "beats") representing a different arrhythmia are recorded and acquired on an additional map or saved to a storage bank.

During a session a patient may exhibit various arrhythmic states. For example the patient may show transitions in various combinations and sub-combinations among sinus rhythm, paroxysmal ventricular contractions, atrial flutter, and ventricular tachycardia. The various arrhythmias affect electroanatomic maps. Embodiments of the invention analyze intracardiac electrograms morphologically to identify beats with the various arrhythmias, and concurrently generate respective electroanatomic maps. The necessity of a separate operation to separate the various morphologies in order to create separate maps corresponding to the respective arrhythmias is avoided.

According to embodiments of the invention multiple maps are automatically created based on respective templates of signal morphologies of the different arrhythmias. The signals used for the preparing the maps may be intracardiac or body surface signals.

In one embodiment a pre-defined template representing a certain arrhythmia is provided. Each beat's morphology can be compared in real time to the template while the user collects data in the heart chambers. The beat is accepted or rejected to the map based on the morphology.

In another embodiment templates of different arrhythmias are prepared adaptively, based on recorded beat morphologies.

There is provided according to embodiments of the invention a method, which is carried out by recording electrograms of a heart of a living subject in a plurality of channels, automatically placing the beats of the electrograms into respective classifications according to a resemblance of the morphologic characteristics of the beats to members of a set of templates, and generating multiple electroanatomic maps of the heart from the beats in the respective classifications.

According to one aspect of the method, recording is performed with a plurality of electrodes to produce multiple respective electrograms.

According to an additional aspect of the method, the set of templates are predefined.

In another aspect of the method placing the beats into respective classifications includes calculating respective overall correlations between instances of a selected beat in all the channels and the members of the set of templates, and associating the selected beat with a member of the set of templates having the highest ranked correlation when the correlation exceeds a predefined correlation threshold.

When none of the overall correlations exceeds the predefined correlation threshold the method is further carried out by creating a new member of the set of templates with the selected beat.

In a further aspect of the method placing the beats into respective classifications is carried out by creating a new member of the set of templates with a selected beat, calculating an overall correlation between instances of the selected beat in all the channels and the new member, and when the overall correlation exceeds a predefined correlation threshold associating the selected beat with the new member.

According to still another aspect of the method, calculating an overall correlation includes calculating respective correlations between the instances of the selected beat in the channels and the new member, and weighting the respective correlations according to maximum signal amplitudes of the instances of the selected beat in the electrograms.

Yet another aspect of the method is carried out when the overall correlation fails to exceed the predefined correlation threshold by shifting a phase of the electrograms, and thereafter iterating the steps of calculating and associating.

There is further provided according to embodiments of the invention an apparatus including a probe having a plurality of electrodes on a distal portion thereof, electrical circuitry for recording respective time-varying electrograms from the electrodes when the probe is at a location in a heart of a living subject, a memory for storing the electrograms, a display, and a processor connected to the memory and operative for recording electrograms of a heart of a living subject in a plurality of channels, automatically placing the beats of the electrograms into respective classifications according to a resemblance of the morphologic characteristics of the beats to members of a set of templates, and generating multiple electroanatomic maps of the heart from the beats in the respective classifications and presenting the maps on the display.

There is further provided according to embodiments of the invention a computer software product, including a non-transitory computer-readable storage medium in which computer program instructions are stored, which instructions, when executed by a computer, cause the computer to perform a method comprising the steps of accepting electrograms of a heart of a living subject in a plurality of channels, automatically placing the beats of the electrograms into respective classifications according to a resemblance of the morphologic characteristics of the beats to members of a set of templates, and generating multiple electroanatomic maps of the heart from the beats in the respective classifications.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein:

FIG. 2 is a flow diagram of a method for preparing electroanatomic maps of the heart in accordance with an embodiment of the invention;

FIG. 3 is a schematic block diagram illustrating operation of a signal analyzing algorithm, according to an embodiment of the invention;

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.
Definitions.

"Annotations" or "annotation points" refer to points of time on an electrogram that are considered to denote events of interest. In this disclosure the events are typically local activation time of the propagation of an electrical wave as sensed by the electrode.

"Activity" in an electrogram is used herein to denote a distinct region of bursty or undulating changes in an electrogram signal. Such a region may be recognized as being outstanding between regions of baseline signals. In this disclosure "activity" more often refers to a manifestation on an electrogram of one or more electrical propagation waves through the heart.

A "wave" refers to continuous electrical propagation within a mapped area of the heart.
Overview.

Figure 1:
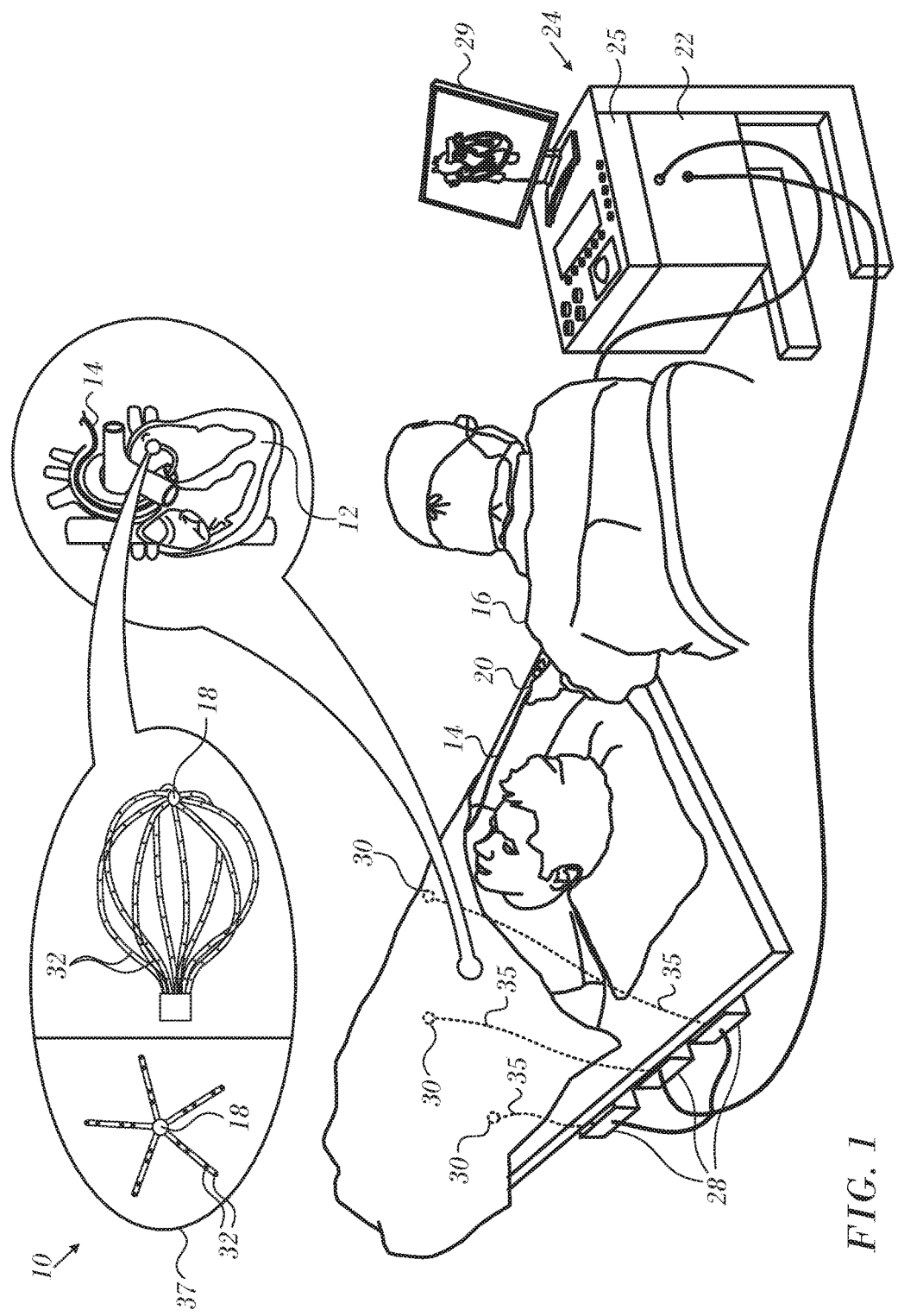
FIG. 1 is a pictorial illustration of a system for evaluating electrical activity in a heart of a living subject in accordance with an embodiment of the invention.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091 and U.S. Patent Application Publication No. 20070197929, entitled Mapping of Complex Fractionated Atrial Electrogram, all of whose disclosures are herein incorporated by reference.

The system 10 may comprise a general purpose or embedded computer processor, which is programmed with suitable software for carrying out the functions described hereinbelow. Thus, although portions of the system 10 shown in other drawing figures herein are shown as comprising a number of separate functional blocks, these blocks are not necessarily separate physical entities, but rather may represent, for example, different computing tasks or data objects stored in a memory that is accessible to the processor. These tasks may be carried out in software running on a single processor, or on multiple processors. The software may be provided to the processor or processors on tangible non-transitory media, such as CD-ROM or non-volatile memory. Alternatively or additionally, the system 10 may comprise a digital signal processor or hard-wired logic. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

The catheter 14 is a typically multi-electrode catheter, which can be a basket catheter as shown in the upper part of balloon 37, or a spline catheter as shown in the lower part. In any case there are multiple electrodes 32, which are used as sensing electrodes and have known locations on the basket or spline, and known relationships to one another. Thus, once the catheter is located in the heart, for example by constructing a current position map, the location of each of the electrodes 32 in the heart is known. One method for generation of a current position map is described in commonly assigned U.S. Pat. No. 8,478,383 to Bar-Tal et al., which is herein incorporated by reference.

Electrical signals can be conveyed to and from the heart 12 from the electrodes 32 located at or near the distal tip 18 of the catheter 14 via cable 34 to the console 24. Pacing signals and other control signals may be conveyed from the console 24 through the cable 34 and the electrodes 32 to the heart 12.

Wire connections 35 link the console 24 with body surface electrodes 30 and other components of a positioning sub-system for measuring location and orientation coordinates of the catheter 14. The processor 22, or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted near the distal tip 18 of the catheter 14.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes as described in further detail below.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally applied reference patch attached to the exterior of the subject's body, or on an internally-placed catheter, which is inserted into the heart 12 and maintained in a fixed position relative to the heart 12. The system 10 may receive image data from an external imaging modality, such as an MRI unit or the like and includes image processors that can be incorporated in or invoked by the processor 22 for generating and displaying images that are described below.

Reference is now made to FIG. 2, which is a high level flow diagram of a method for preparing electroanatomic maps of the heart in accordance with an embodiment of the invention. The process steps are shown in a particular linear sequence in FIG. 2 and the other flowcharts herein for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method.

At initial step 39 the heart is catheterized conventionally, usually, but not necessarily, with a multi-electrode mapping catheter. Catheters such as the PentaRay® NAV or Navistar® Thermocool® catheters, available from Biosense Webster, are suitable for initial step 39. The electrodes of the catheter are placed in galvanic contact with respective locations in one of the heart chambers. Additionally or alternatively ECG readings may be recorded.

Next, at step 41 intracardiac electrograms are recorded and annotated with the multiple electrodes of the catheter, each having a respective location, which can be determined using the position tracking capabilities of the system 10 (FIG. 1). The recordings may be obtained and processed concurrently. The electrograms may be recorded and data collected throughout a catheterization session as the catheter is navigated within the heart. Additionally or alternatively the data may be collected in a "hunting mode", wherein the catheter is stable in a location, and the operator awaits rhythm changes generally, or the appearance of a particular arrhythmia. The data may be collected using unipolar or bipolar electrode configurations.

Annotation of the intracardiac electrograms may be performed using the teachings of commonly assigned U.S. Patent Application Publication No. 20150073246, entitled Method for Mapping Ventricular/Atrial Premature Beats During Sinus Rhythm, U.S. Pat. No. 9,380,953, entitled Hybrid Bipolar/Unipolar Detection of Activation Wavefront, and U.S. Patent Publication No. 20150208942, entitled Double Bipolar Configuration for Atrial Fibrillation Annotation, which are herein incorporated by reference.

Next, beat acquisition step 43 is performed. Step 43 comprises template selection step 45, and template matching step 47, in which the morphology of the intracardiac electrograms is automatically matched to the templates beat-by-beat. Step 43 also comprises step 49 in which the classified beat data is accumulated in respective storage.

Then, at final step 51 a functional electroanatomic map, e.g., an LAT map, is automatically generated for each class that was identified in step 43.

Arrhythmia Identification.

During a session a patient may exhibit various arrhythmic states. For example the patient may show transitions in various combinations and sub-combinations among sinus rhythm, paroxysmal ventricular contractions, atrial flutter, and ventricular tachycardia. The various arrhythmias affect electroanatomic maps. Embodiments of the invention analyze intracardiac electrograms morphologically to identify beats with the various arrhythmias, detect all the morphologic templates and concurrently generate respective electroanatomic maps. Each map comprises morphologic beats that correspond to a respective template and thus represents the same arrhythmia.

Reference is now made to FIG. 3, which is a schematic block diagram illustrating operation of a signal analyzing algorithm, according to an embodiment of the invention. The algorithm morphologically identifies beats with a template representing a cardiac arrhythmia. The algorithm is executed by a processor 53. Input data comprising processed signals 55 obtained from a body surface electrode or internal unipolar or bipolar electrode. The input data includes reference annotations 57, patterns 59, and correlation thresholds 61, all inputs being submitted to a morphology matching filter 63. The outputs of the algorithm comprise accepted beats 65, correlations 67 of the beats with a single channel and an overall amplitude-weighted correlation 69. The outputs may be presented on a display 71. In some applications the correlation calculations can be performed continuously by moving the template with respect to the ECG signals, rather than positioning the template around pre-determined discrete points.

Figure 4:
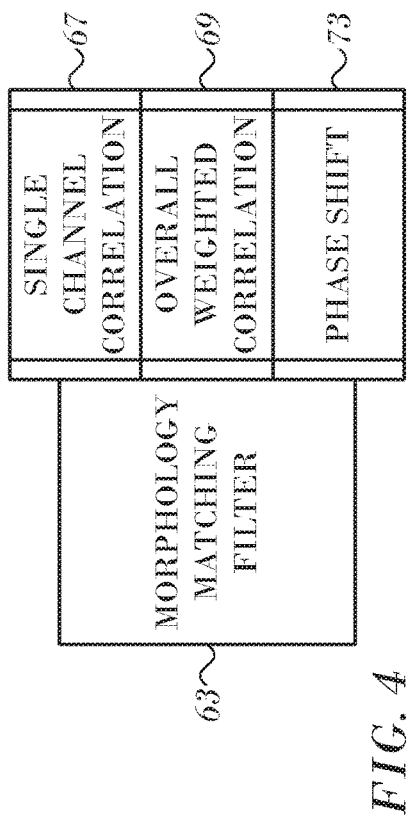
FIG. 4 is a block diagram of a morphology matching filter in accordance with an embodiment of the invention.

Reference is now made to FIG. 4, which is a detailed block diagram of the morphology matching filter 63 (FIG. 3) in accordance with an embodiment of the invention. The filter 63 produces the single channel correlations 67, the overall weighted correlation 69 and a phase shift indicator 73

Figure 5:
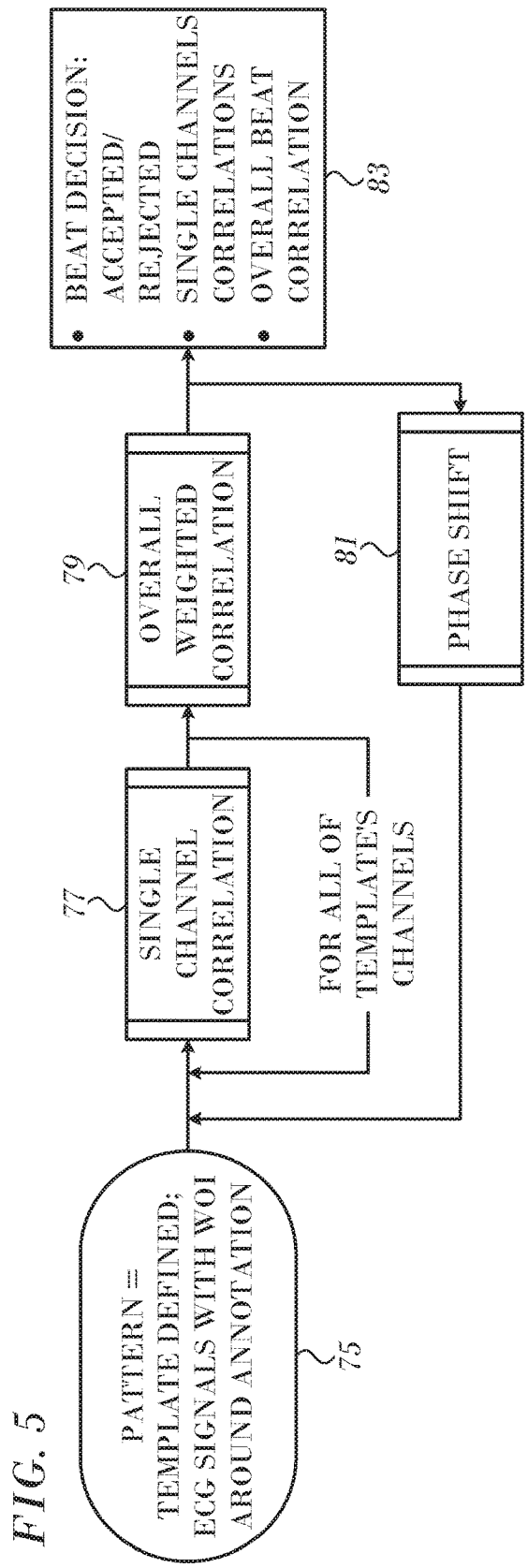
FIG. 5 is detailed block diagram of the filter shown in FIG. 4 in accordance with an embodiment of the invention.

Reference is now made to FIG. 5, which is a more detailed block diagram of the filter 63 (FIG. 4) in accordance with an embodiment of the invention. A pattern template is input at block 75 together with electrograms. The template i is prepared automatically and adaptively from the electrode readings. A window of interest defining a beat is automatically defined, using known methods, about an annotation in each electrogram.

Then at block 77 single channel correlations are made between each of the template channels and each of the electrograms input at block 75.

Next, at block 79 an overall weighted correlation between the electrograms and the template is calculated. Details are presented below in the discussion of FIG. 7.

At block 81 a phase shift is fed back to the input of block 77 and the iterations repeated with the phase-shifted signal in order to maximize the weighted correlation in block 79, as explained in further detail below. The phase-shifted signal may be applied either to the template, or the electrode data.

Finally, in block 83 a decision is made to accept or reject the beat and to report the correlations obtained in block 79.

Figure 6:
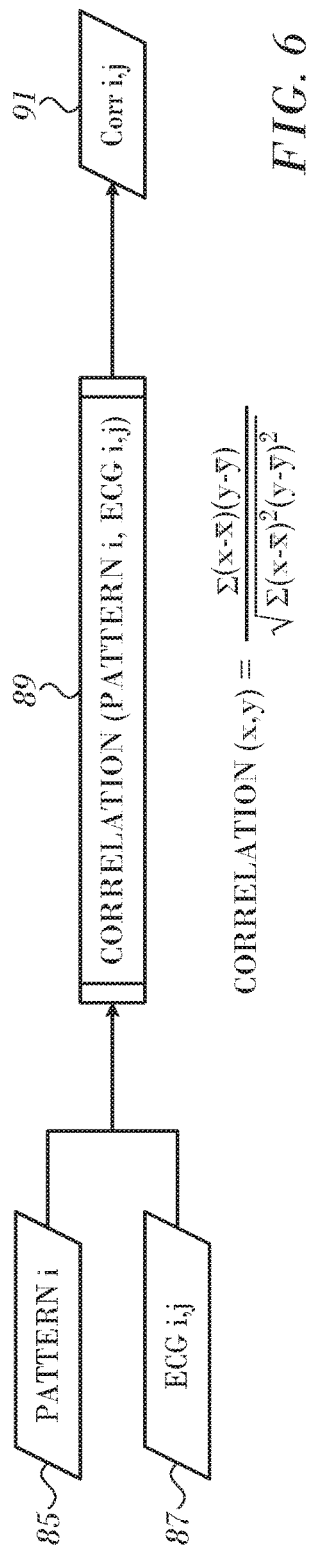
FIG. 6 is a graphical representation of a correlation calculation in accordance with an embodiment of the invention.

Reference is now made to FIG. 6, which is a graphical representation of the calculation in block 77 (FIG. 5). In block 85 For each template (denoted as pattern i), and each electrogram in block 87 a correlation is calculated in block 89 using the indicated correlation formula. The result is output in block 91.

Figure 7:
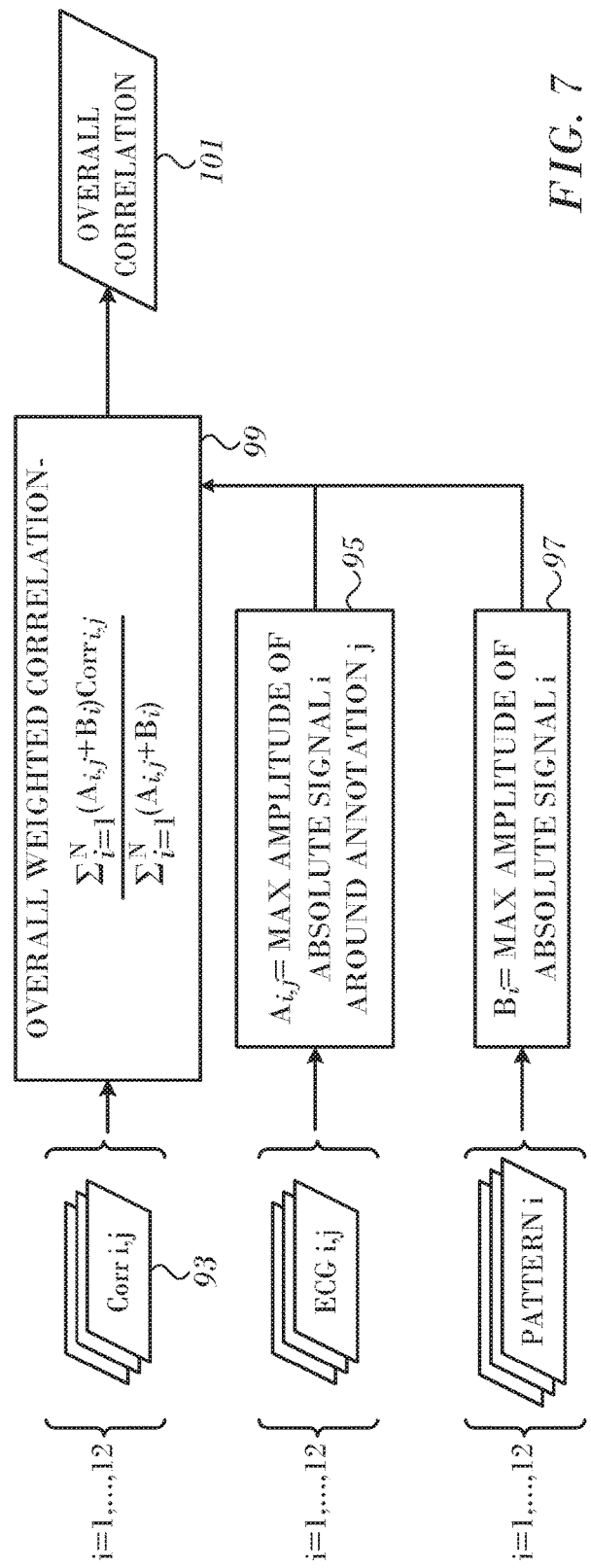
FIG. 7 is a graphical representation of an overall weighted correlation in accordance with an embodiment of the invention.

Reference is now made to FIG. 7, which is a graphical representation of the calculation of the overall weighted correlation (correlation 69, FIG. 4; block 79, FIG. 5). A 12-lead electrocardiogram as assumed by way of example. However the method is applicable to any number of electrodes, for example, in a multi-electrode catheter as described above.

The correlations obtained from multiple leads that are output in block 91 (FIG. 6) are represented by blocks 93. The absolute values of the amplitudes of the ECG channels at their annotations and throughout the cardiac cycle are represented by blocks 95, 97, respectively. An overall weighted correlation is calculated in block 99 using the inputs from blocks 93, 95, 97, using the formula shown. The result is output in block 101.

Figure 8:
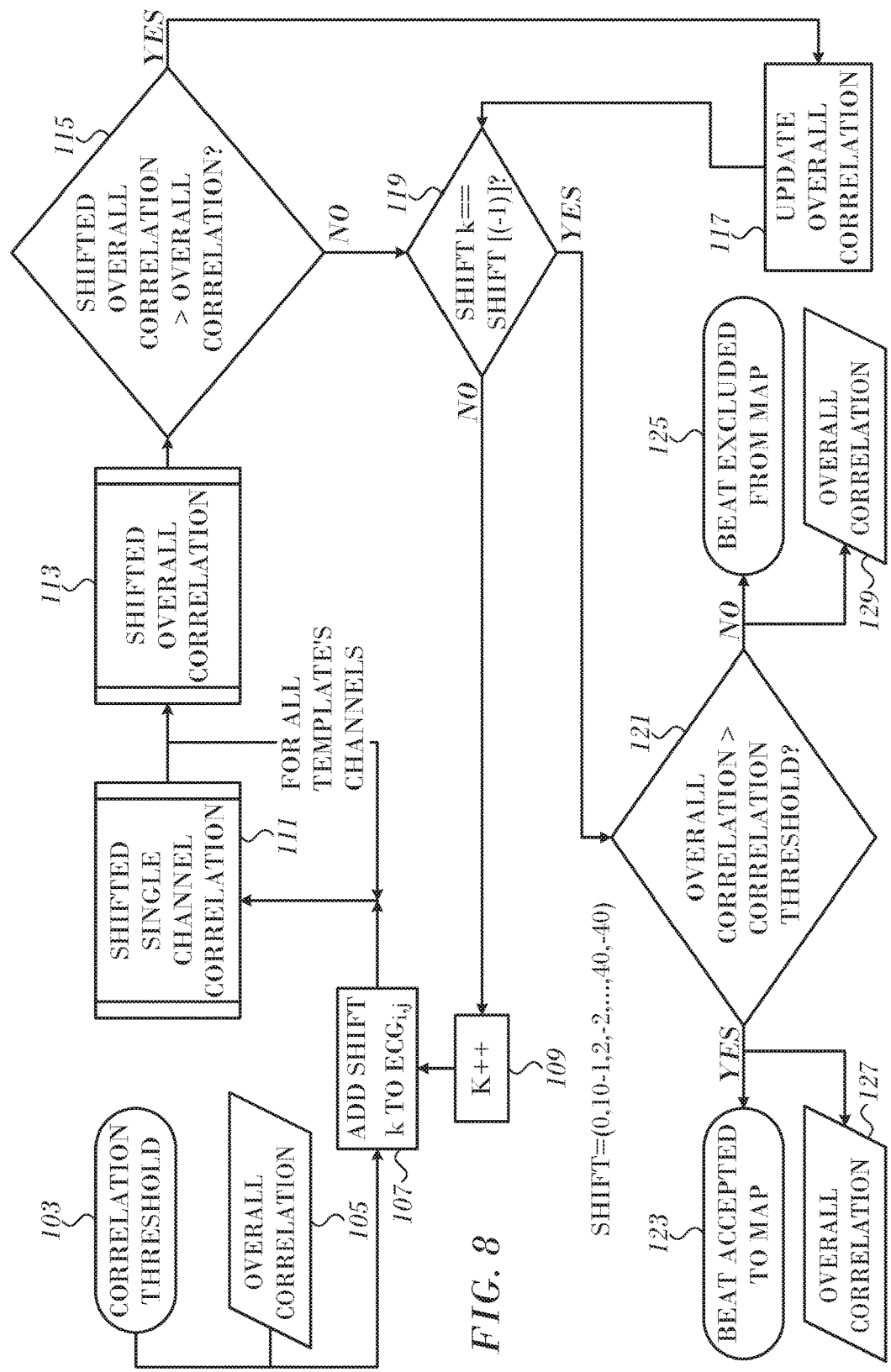
FIG. 8 is a graphical representation of a method for introducing phase shifts into a cyclic cardiac electrogram in accordance with an embodiment of the invention.

Reference is now made to FIG. 8, which is a detailed graphical representation of the feedback represented by block 81 (FIG. 5) that produces a phase shift in each of the individual electrograms so as to optimize the overall weighted correlation (FIG. 7). A predefined correlation threshold represented by block 103 is compared with the overall correlation 69 (FIG. 4), represented in FIG. 8 by block 105. The result is added in block 107 to a phase shift (k) (block 109), which is described below. If the correlation threshold has not been achieved, the phase of all the channels is shifted and used in the next iteration of the correlation algorithm to produce new correlations for the single channels, and a new overall correlation in blocks 111, 113. The phase-shifted signals may be applied either to the template, or the electrode data.

At block 115 it is determined if the shifted overall correlation produced in block 113 is better than the overall correlation obtained in the previous iteration of the feedback loop. If so then the overall correlation is updated in block 117.

If not, or after the update in block 117 in a decision block 119 it is determined if the number of loop iterations has reached a predetermined limit. If the value of the current phase has not reached the limit, then a phase shift is performed in block 109 and the loop iterated.

Otherwise, in decision block 121 it is determined if the current value of the overall correlation exceeds the correlation threshold input in block 103. If so the current cardiac cycle beat is accepted in the corresponding map in block 123. If not, then the current beat is rejected and excluded from the map in block 125. In any case the current value of the overall correlation is reported in one of blocks 127, 129.
Multiple Map Creation.

Figure 9:
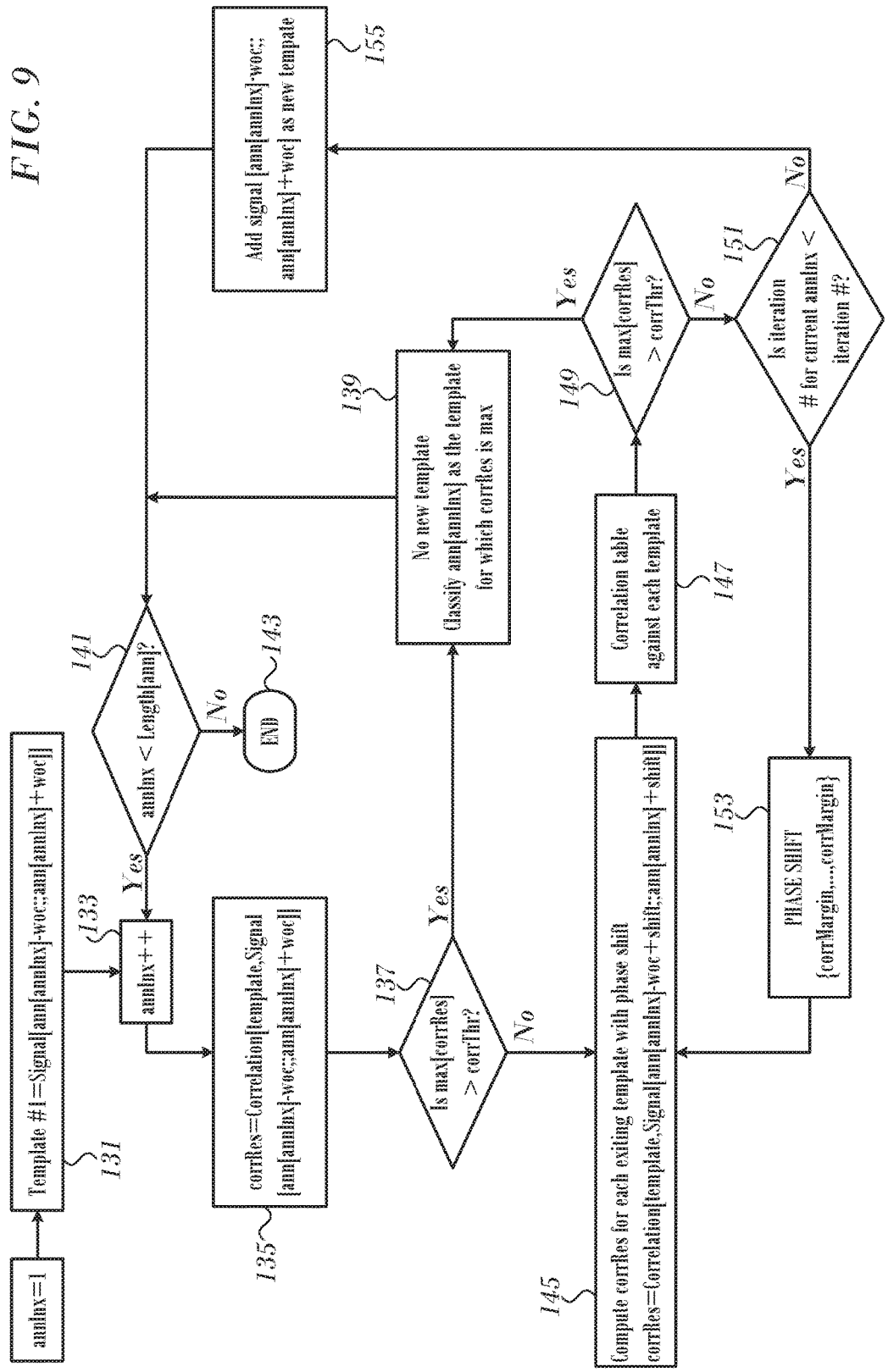
FIG. 9 is a flow chart of a method of multiple electroanatomic map creation in accordance with an embodiment of the invention.

Reference is now made to FIG. 9, which is a flow chart of a method of multiple electroanatomic map creation in accordance with an embodiment of the invention. As noted above in the discussion of FIG. 2, a parallel implementation may be chosen in order that the algorithm be performed in near real time. It is assumed that beats from multiple electrodes are accumulated and annotated. Typically, instances of the process shown in FIG. 9 are performed concurrently for respective channels. Annotation and accumulation of the beats as described above (FIG. 3; FIG. 5) may occur concurrently with the process of FIG. 9. Alternatively, steps of the process may be performed off-line, concurrently or sequentially for different channels in many combinations. In this embodiment templates are created dynamically, according to the morphologic patterns of a particular patient. Newly accumulated beats are then correlated with the templates.

In initial step 131 one of the templates is selected as a reference template and becomes the first member of a set of templates. This set may be augmented under conditions that are described below.

Next, at step 133 a time interval, i.e., a window of correlation from the channel is selected. Correlation of the current time interval with the reference template is calculated in step 135 as described above in the discussion of FIG. 6.

Next, at decision step 137, it is determined if the correlation that was calculated in step 135 exceeds a predefined correlation threshold. If the determination at decision step 137 is affirmative, then control proceeds to step 139. The beat is classified in accordance with the reference template that was chosen in initial step 131. The current beat is accumulated for creation of an electroanatomic map to be created using known methods.

Next, at decision step 141, it is determined if more beats in the channel remain to be processed. If the determination at decision step 141 is negative, then control proceeds to final step 143 and the procedure terminates. If the determination at decision step 141 is affirmative, then control returns to step 133 to iterate with another beat.

If the determination at decision step 137 is negative, then control proceeds to step 145. A phase shift is introduced (block 81; FIG. 5) and correlations are computed between the phase-shifted beat and the reference template, and between the phase-shifted beat and all other members of the set of templates that have been introduced in previous iterations of the process or other instances of the process.

Next, at step 147 the correlations calculated in step 145 are ranked. Then at decision step 149, it is determined if the predetermined correlation threshold is exceeded by the highest ranked correlation. If the determination at step 149 is affirmative, then control proceeds to step 139 for classification of the beat in accordance with the most highly correlated template.

If the determination at step 149 is negative, then, at decision step 151, it is determined whether iterations of step 145 remain to be performed with the current beat before a maximum number of phase shifts is exceeded. If the determination at decision step 151 is affirmative, then a new phase shift is introduced in step 153, after which control returns to step 145.

If the determination at decision step 151 is negative, then at step 155 it is concluded that the current beat lacks sufficient correlation with any existing template. A new type of arrhythmia may have appeared. A new template is created from the current beat and added to the set of templates to be evaluated in subsequent iterations. Control then proceeds to decision step 141, which was described above. It will be evident that as new arrhythmias become evident in the intracardiac electrograms, they will generally lack correlation with existing templates, and are then added to the set of templates. The set of templates thus forms a dynamic library that is accessible to this instance and other instances of the process that are being performed with other channels.

EXAMPLE

Figure 10:
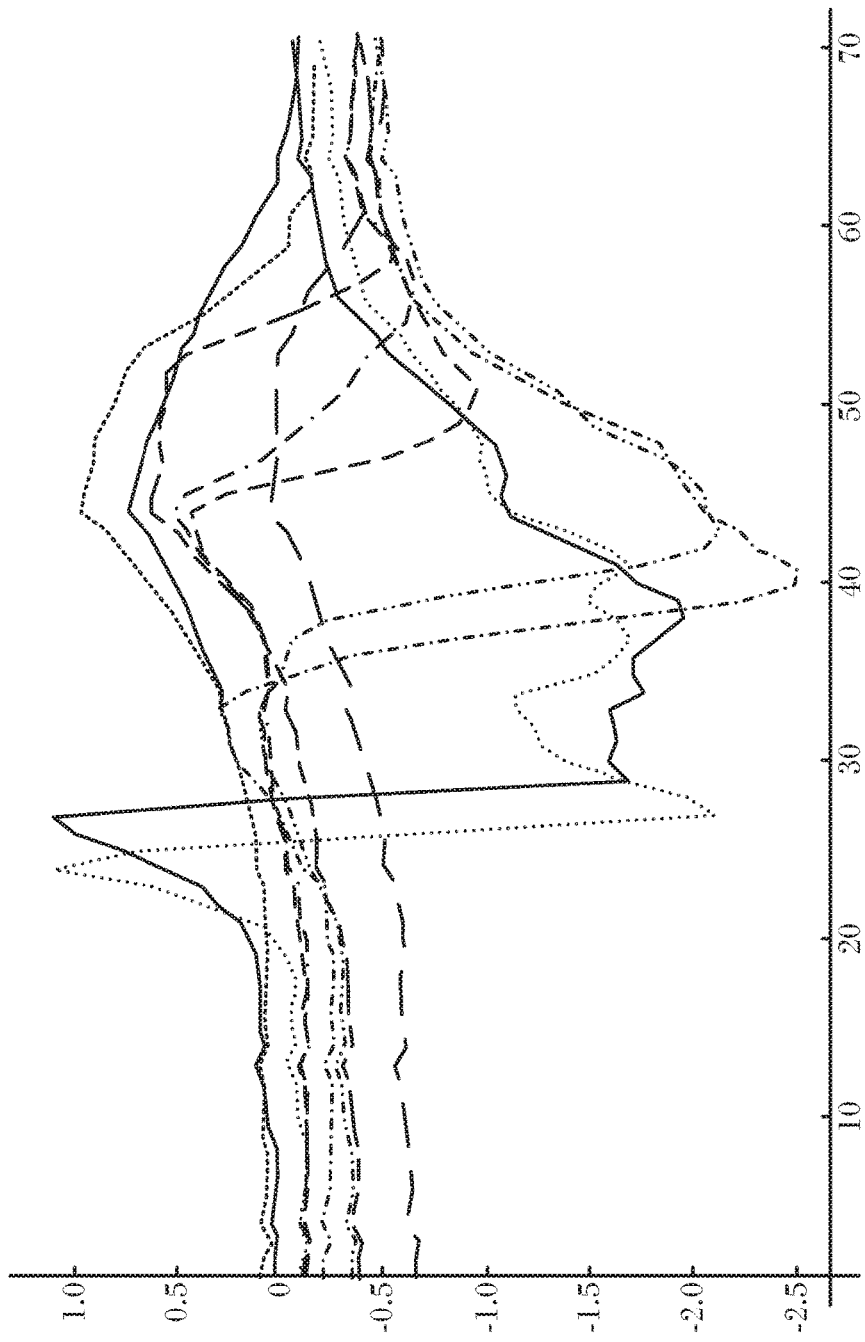
FIG. 10 is a diagram of a group of beats obtained from intracardiac electrograms, which are analyzed in accordance with an embodiment of the invention.

The algorithm summarized in the high level diagram of FIG. 2 results in a mapping of specific arrhythmias based on the morphology of intracardiac electrograms. Reference is now made to FIG. 10, which is a group tracings comprising beats obtained from electrograms, which are analyzed in accordance with an embodiment of the invention.

Figure 11:
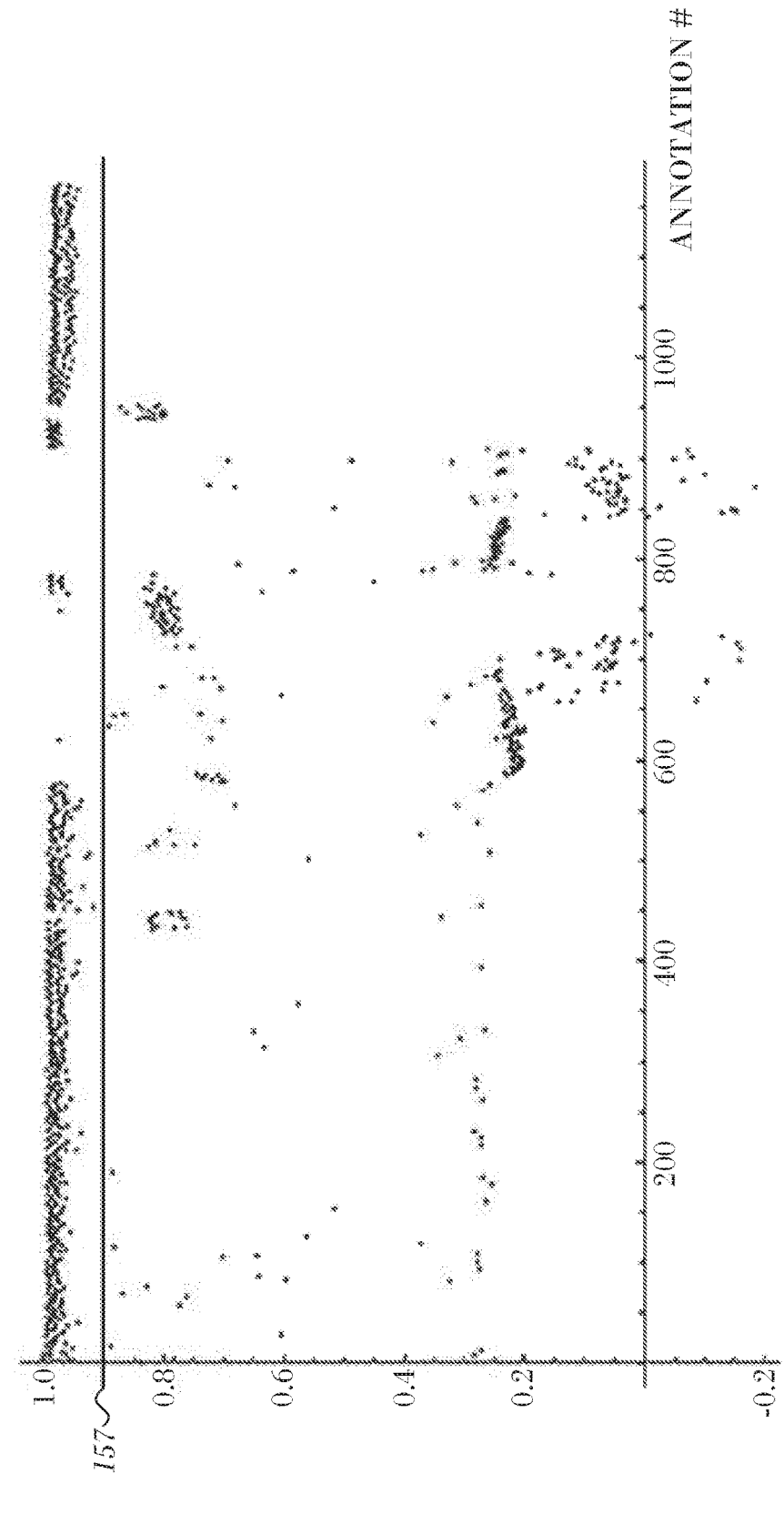
FIG. 11 is a graph illustrating correlations between the electrograms shown in FIG. 10 and a reference template that was selected in accordance with an embodiment of the invention.

Reference is now made to FIG. 11 and again to FIG. 2. FIG. 11 is a plot illustrating the correlations between the electrograms shown in FIG. 10 and a reference template that was selected in accordance with an embodiment of the invention (step 45). The correlations were obtained using the above-described algorithm (FIG. 3-FIG. 8). The morphology of the signals beats of each electrogram is matched (step 47) against the morphology pattern of an automatically chosen reference template. Beats with a high correlation score (at least 0.85) are considered to represent the same arrhythmia. In FIG. 11 there are total of 1173 data points. Of these 767 data points lie above line 157 and represent the same arrhythmia.

As noted above, instances of beats are accumulated (step 49) and incorporated into a respective map derived from the correlated beats occurring during the particular arrhythmia (final step 51).

The procedure is repeated with additional selected templates that respectively characterize other arrhythmias found in the electrograms of FIG. 10.
First Alternate Embodiment.

Referring again to FIG. 9, in this embodiment one or more templates representing particular arrhythmias are prepared in advance. Initial step 131 is modified to begin the process with a set of reference templates from the prepared templates, rather than create an initial reference template with the first beat as described in the previous embodiment.
Second Alternate Embodiment.

The correlation procedures described above in FIG. 5-FIG. 7 may be replaced by other comparisons between an annotation and a template, e.g., Pearson's correlation, the sum of absolute differences, and mean absolute deviation.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the steps of:
recording electrograms of a heart of a living subject in a plurality of channels, the electrograms comprising a plurality of beats having morphologic characteristics;
automatically placing the beats into respective classifications according to a resemblance of the morphologic characteristics of the beats to members of a set of templates by calculating respective overall correlations between instances of a selected beat in all the channels and the members of the set of templates and associating the selected beat with a member of the set of templates having a highest ranked one of the overall correlations when the highest ranked one of the overall correlations exceeds a predefined correlation threshold; and
concurrently generating multiple electroanatomic maps of the heart from the beats in the respective classifications.

2. The method according to claim 1, wherein recording is performed with a plurality of electrodes to produce multiple respective electrograms.

3. The method according to claim 1, wherein the set of templates comprises predefined templates.

4. The method according to claim 1, further comprising the steps of:
when none of the overall correlations exceeds the predefined correlation threshold creating a new member of the set of templates with the selected beat.

5. The method according to claim 1, wherein placing the beats into respective classifications comprises the steps of:
creating a new member of the set of templates with a selected beat;
calculating an overall correlation between instances of the selected beat in all the channels and the new member; and
when the overall correlation exceeds a predefined correlation threshold associating the selected beat with the new member.

6. The method according to claim 5, wherein calculating an overall correlation comprises:
calculating respective correlations between the instances of the selected beat in the channels and the new member; and
weighting the respective correlations according to maximum signal amplitudes of the instances of the selected beat in the electrograms.

7. The method according to claim 5, further comprising:
when the overall correlation fails to exceed the predefined correlation threshold:
shifting a phase of the electrograms; and
thereafter iterating the steps of calculating and associating.

8. An apparatus comprising:
a probe having a plurality of electrodes on a distal portion thereof;
electrical circuitry for recording respective time-varying electrograms from the electrodes when the probe is at a location in a heart of a living subject;
a memory for storing the electrograms;
a display; and
a processor connected to the memory and operative for performing the steps of:
recording the electrograms in a plurality of channels, the electrograms comprising a plurality of beats having morphologic characteristics;
automatically placing the beats into respective classifications according to a resemblance of the morphologic characteristics of the beats to members of a set of templates by calculating respective overall correlations between instances of a selected beat in all the channels and the members of the set of templates and associating the selected beat with a member of the set of templates having a highest ranked one of the overall correlations when the highest ranked one of the overall correlations exceeds a predefined correlation threshold; and
concurrently generating multiple electroanatomic maps of the heart from the beats in the respective classifications; and
presenting the maps on the display.

9. The apparatus according to claim 8, wherein the set of templates comprises predefined templates.

10. The apparatus according to claim 8, wherein the processor is operative for performing the step of:
when none of the overall correlations exceeds the predefined correlation threshold creating a new member of the set of templates with the selected beat.

11. The apparatus according to claim 8, wherein placing the beats into respective classifications comprises the steps of:
creating a new member of the set of templates with a selected beat;
calculating an overall correlation between instances of the selected beat in all the channels and the new member; and
when the overall correlation exceeds a predefined correlation threshold associating the selected beat with the new member.

12. The apparatus according to claim 11, wherein calculating an overall correlation comprises:
calculating respective correlations between the instances of the selected beat in the channels and the new member; and
weighting the respective correlations according to maximum signal amplitudes of the instances of the selected beat in the electrograms.

13. The apparatus according to claim 11, wherein the processor is operative for performing the steps of:
when the overall correlation fails to exceed the predefined correlation threshold:
shifting a phase of the electrograms; and
thereafter iterating the steps of calculating and associating.

14. A computer software product, including a non-transitory computer-readable storage medium in which computer program instructions are stored, which instructions, when executed by a computer, cause the computer to perform the steps of:
accepting electrograms of a heart of a living subject in a plurality of channels, the electrograms comprising a plurality of beats having morphologic characteristics;
automatically placing the beats into respective classifications according to a resemblance of the morphologic characteristics of the beats to members of a set of templates by calculating respective overall correlations between instances of a selected beat in all the channels and the members of the set of templates and associating the selected beat with a member of the set of templates having a highest ranked one of the overall correlations when the highest ranked one of the overall correlations exceeds a predefined correlation threshold; and
concurrently generating multiple electroanatomic maps of the heart from the beats in the respective classifications.

15. The computer software product according to claim 14, wherein the computer is further instructed to perform the steps of:
when none of the overall correlations exceeds the predefined correlation threshold creating a new member of the set of templates with the selected beat.

16. The computer software product according to claim 14, wherein placing the beats into respective classifications comprises the steps of:
creating a new member of the set of templates with a selected beat;
calculating an overall correlation between instances of the selected beat in all the channels and the new member; and
when the overall correlation exceeds a predefined correlation threshold associating the selected beat with the new member.

17. The computer software product according to claim 16, wherein calculating an overall correlation comprises:
calculating respective correlations between the instances of the selected beat in the channels and the new member; and
weighting the respective correlations according to maximum signal amplitudes of the instances of the selected beat in the electrograms.

18. The computer software product according to claim 16, further comprising:
when the overall correlation fails to exceed the predefined correlation threshold:
shifting a phase of the electrograms; and
thereafter iterating the steps of calculating and associating.

* * * * *